(12) United States Patent
Di Ubaldi

(10) Patent No.: US 11,235,134 B2
(45) Date of Patent: Feb. 1, 2022

(54) NEURAXIAL CONNECTOR

(71) Applicant: Becton, Dickinson and Company, Franklin Lakes, NJ (US)

(72) Inventor: John Di Ubaldi, Jackson, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 312 days.

(21) Appl. No.: 16/032,156

(22) Filed: Jul. 11, 2018

(65) Prior Publication Data

US 2020/0016391 A1    Jan. 16, 2020

(51) Int. Cl.
*A61M 39/10*    (2006.01)

(52) U.S. Cl.
CPC ..... *A61M 39/10* (2013.01); *A61M 2039/1077* (2013.01); *A61M 2039/1094* (2013.01)

(58) Field of Classification Search
CPC .................. A61M 39/24; A61M 39/10; A61M 2039/1077; A61M 2039/1094
See application file for complete search history.

(56) References Cited

U.S. PATENT DOCUMENTS

| | | | |
|---|---|---|---|
| 2009/0099552 A1 | 4/2009 | Levy et al. | |
| 2012/0330238 A1* | 12/2012 | Robert | A61M 5/14 604/151 |
| 2015/0157848 A1* | 6/2015 | Wu | A61J 1/2096 604/513 |
| 2015/0290421 A1 | 10/2015 | Glickman et al. | |
| 2016/0310721 A1* | 10/2016 | Lesser | A61M 5/3216 |

OTHER PUBLICATIONS

Medzus, "Epidural Kit (Type-I)", Apr. 29, 2017 (Year: 2017).*
PCT International Search Report and Written Opinion in PCT/US2019/064946 dated Feb. 28, 2020, 14 pages.
PCT International Search Report and Written Opinion in PCT/US2019/040915 dated Sep. 23, 2019, 14 pages.
International Standard "Small bore connectors for liquids and gases in healthcare applications—Part 6: Connectors for neuraxial applications", ISO 80369-6, First Edition, Mar. 15, 2016, 8 pages.
Non-Final Office Action in U.S. Appl. No. 16/704,435, dated Sep. 30, 2020, 14 pages.

* cited by examiner

*Primary Examiner* — Bhisma Mehta
*Assistant Examiner* — John J Crawford
(74) *Attorney, Agent, or Firm* — Servilla Whitney LLC

(57) ABSTRACT

Described is a medical adapter assembly comprising an end including a neuraxial fitting that is not directly connectable to a standard luer fitting, an opposing end including a standard luer fitting connectable to a standard luer fitting of an intravenous medical device, and a check valve that allows fluid flow from the end with the standard luer fitting to the end with the neuraxial fitting, but prevents fluid flow from the end with the neuraxial fitting to the end with the standard luer fitting. Methods of using the medical adapter assembly and kits containing the medical adapter assembly are also described.

15 Claims, 9 Drawing Sheets

NEURAXIAL CONNECTOR

TECHNICAL FIELD

Aspects of the present disclosure relate to a medical adapter assembly that enables connection of a neuraxial device to a device having a standard luer fitting.

BACKGROUND

Current anesthesia procedures use general purpose syringes attached to spinal or epidural needles. The interface connection between the syringe and the needle is governed by International Organization for Standardization (ISO) 80369-7 or a standard "Luer" connection. As an example, for a typical epidural blood patch procedure, the same syringe is utilized to directly draw blood from or via an existing intravenous medical device, as well as to administer the drawn blood to the patient's epidural space.

ISO 80369-7:2016 defines a specification for standard Luer connectors including a 6% taper between the distal end and the proximal end. A male standard luer connector increases from the open distal end to the proximal end. A female standard luer connector decreases from the open proximal end to the distal end. According to ISO 80369-7: 2016, a male standard luer connector has an outer cross-sectional diameter measured 0.75 mm from the distal end of the tip of between 3.970 mm and 4.072 mm. The length of the male standard luer taper is between 7.500 mm to 10.500 mm. The outer cross-sectional diameter measured 7.500 mm from the distal end of the tip is between 4.376 mm and 4.476 mm. As used herein, the phrases "male standard luer connector" and "female standard luer connector" shall refer to connectors having the dimensions described in ISO 80369-7, which is hereby incorporated by reference in its entirety.

The convenience and near-universal adoption of the Luer connection presents the opportunity for a multitude of misconnection/wrong-route administration incidents. A problem is the risk of wrong-route administration of medications made possible by the use of identical connections for very different targeted applications (e.g., the use of Luer connections for unrelated delivery systems—vascular, enteral, respiratory, epidural, and intrathecal). As a result, care providers can inadvertently connect the wrong systems together, causing fluid (e.g. medications, enteral feedings) or gases (e.g. oxygen) to be delivered through an incorrect route. In this regard, reports can be found for the unintended neuraxial administration of virtually any drug intended for intravenous administration, and vice versa, for the unintended intravenous administration of drugs intended for neuraxial administration. Such mishaps can result in catastrophic consequences. For example, in 2007, there were four incidents where the chemotherapy medication vincristine was accidently administered by an intrathecal route instead of by the intended intravenous route.

In response, the International Organization for Standardization (ISO) developed standards for small-bore connectors for medical uses. In 2016, ISO standard, "EN ISO 80369-6:2016/ISO 80369-6:2016: Small-bore connectors for liquids and gases in healthcare applications—Part 6: Connectors for Neuraxial Applications" was developed to address the importance of preventing misconnection between small-bore connectors used in different medical applications. ISO 80369-6 dictates both the female (needle side) and male (syringe side) connector dimensions and geometries. This ISO 80369-6 standard also results in a situation where a neuraxial syringe is incompatible with a device having a standard luer connector in compliance with ISO 80369-7. Accordingly, a syringe compliant with the ISO 80369-6 will not misconnect to a needle hub compliant with the ISO 80369-7 standard.

Limiting the use of standard luer tips and connectors to use with vascular access systems is one consensus accepted by device manufacturers and regulatory bodies. The recent adoption of ISO 80369-6 provides a uniform standard for small bore connectors for neuraxial applications. However, the adoption of ISO 830369-6 has complicated the ability to complete certain anesthetic procedures using currently available medical devices, in particular, neuraxial anesthetic procedures, such as spinal anesthesia and epidural anesthesia. It would be desirable to provide connectors, methods, and kits that would facilitate anesthetic procedures with existing medical devices.

SUMMARY

A first aspect of the present disclosure pertains to a medical adapter assembly. In one or more embodiments, a medical adapter assembly comprises a first end comprising a neuraxial fitting that is not directly connectable to a standard luer fitting; a second end opposite the first end, the second end comprising a standard luer fitting connectable to a standard luer fitting of an intravenous medical device; and a check valve that allows fluid flow from the second end to the first end and prevents fluid flow from the first end to the second end.

A second aspect of the present disclosure pertains to a method. In one or more embodiments, a method comprises connecting a syringe comprising a syringe barrel and a distal tip including a neuraxial fitting that is not directly connectable to a standard luer fitting to a medical adapter assembly having a first end comprising a neuraxial fitting, a second end opposite the first end, the second end comprising a luer fitting that is not directly connectable to a neuraxial fitting, and a check valve that prevents fluid flow from the first end to the second end; disconnecting the medical adapter assembly from the syringe; and connecting the neuraxial fitting to a neuraxial needle.

Another aspect of the present disclosure pertains to a kit. In one more embodiment, a kit comprises a medical adapter assembly; a syringe; and a needle. In one or more embodiments, the medical adapter assembly comprises a first end comprising a neuraxial fitting that is not directly connectable to a standard luer fitting; a second end opposite the first end, the second end comprising a standard luer fitting connectable to a standard luer fitting of an intravenous medical device; and a check valve that allows fluid flow from the second end to the first end and prevents fluid flow from the first end to the second end. In one or more embodiments, the syringe comprising a distal tip including a neuraxial fitting that is not directly connectable to a standard luer fitting. In one or more embodiments, the needle is selected from a spinal needle and an epidural needle.

DETAILED DESCRIPTION

Figure 1:
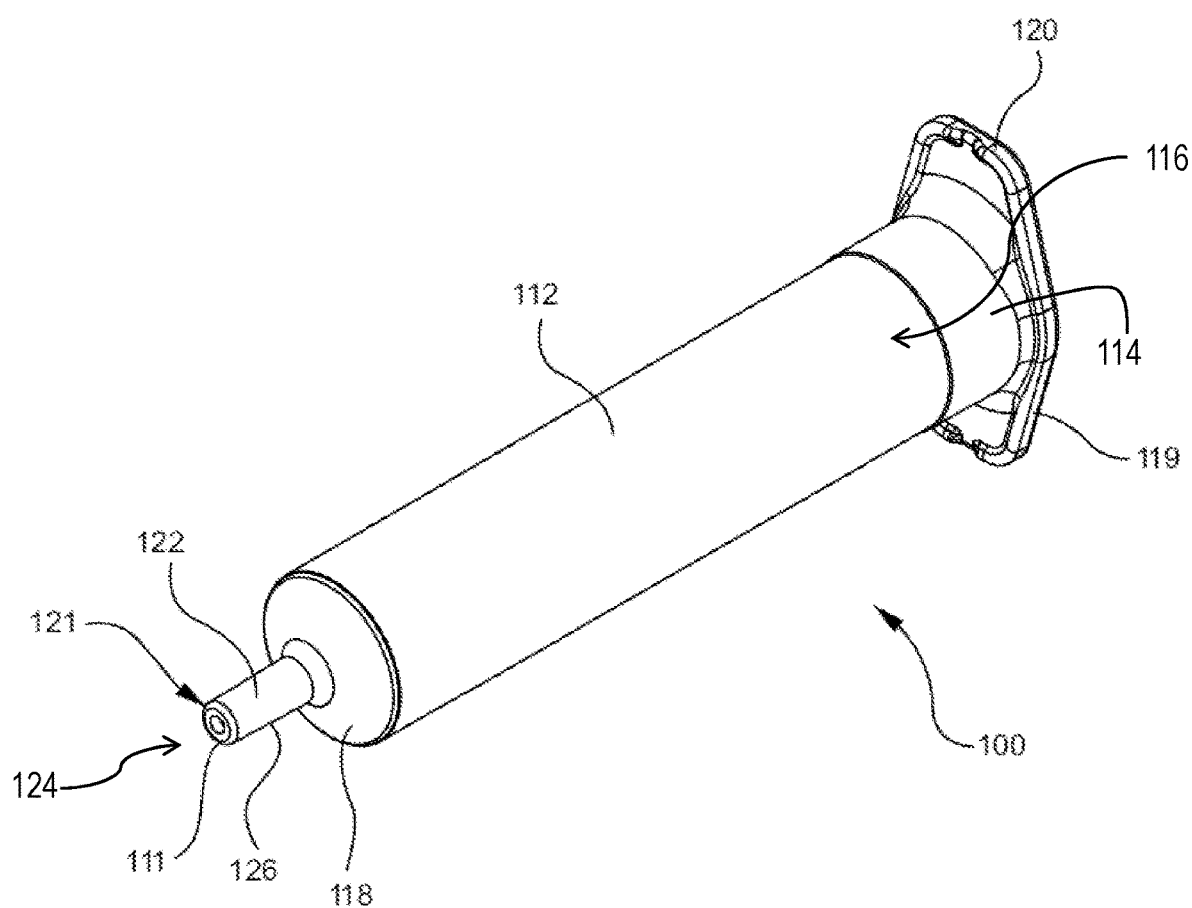
FIG. 1 illustrates a perspective view of a syringe barrel according to one or more embodiment.

Before describing several exemplary embodiments of the disclosure, it is to be understood that the disclosure is not limited to the details of construction or process steps set forth in the following description. The disclosure is capable of other embodiments and of being practiced or being carried out in various ways.

In this disclosure, a convention is followed wherein the distal end of the device is the end closest to a patient and the proximal end of the device is the end away from the patient and closest to a practitioner or care-giver.

As used herein, the term "not connectable" with respect to male and female connectors refers to a connector having a shape, size, dimension, or structure that prevents connection to another connector. For example, a female luer connector has a shape, size, dimension and/or structure that prevents it from forming a connection with a male non-luer connector and is, thus, not connectable with respect to the male non-luer connector. Such a female luer connector, however, has a shape, size, dimension and/or structure that permits connection with a male luer connector and is, thus, connectable with respect to the male luer connector. In another example, a female non-luer connector has a shape, size, dimension and/or structure that prevents connection with a male luer connector and is, thus, not connectable with respect to the male luer connector. Such a female non-luer connector has a shape, size dimension and/or structure that permits connection with a male non-luer connector and is thus connectable connector with respect to the male non-luer connector.

As used herein, the term "not directly connectable" means that there is no intervening device between two fittings. For example, in one or more embodiments, a medical adapter assembly comprises a first end comprising a neuraxial fitting that is not directly connectable to a standard luer fitting. Thus, there is no intervening device between the neuraxial fitting and the standard luer fitting.

As used herein, the term "dimension" shall include the length, diameter, or width of a geometric shape or the geometrically shaped components described herein. The term "cross-sectional diameter" shall include the measurement of the longest distance or greatest distance between two points on an edge of a cross-section of an object or component with a circular or non-circular cross-section.

The two points may be located on the inside surface or outside surface of the edge of the cross-section of the object. The cross-sectional diameter of two points located on the inside surface of the edge of the cross-section of the object shall be referred to as the "inside cross-sectional diameter" and the cross-sectional diameter of two points located on the outside surface of the edge of the cross-section of an object shall be referred to as the "outside cross-sectional diameter." It should be recognized that "cross-sectional diameter" of objects having a circular cross-section may be referred to as the "cross-sectional dimension" or "diameter" of the object. The terms "cross-sectional dimension," "cross-sectional diameter" and "diameter" may be used interchangeably for objects having a circular cross-section.

Syringes are used to deliver fluids for a variety of medical applications, including, for example, oral delivery of nutrients, storage, and delivery of fluid to enteral systems by connecting the syringe to an enteral connection, and intravenous delivery of fluids or medication. Delivery of medication through intravenous syringes involves connecting the distal end of a syringe to a catheter by a luer connection.

Standard luer connectors, as used herein, may include needle hubs, syringes, or other delivery components that incorporate a standard luer connector. FIG. 1 illustrates a syringe barrel 100 having a distal end 111 and a proximal end 119. The syringe barrel 100 includes a sidewall 112 that extends from the distal end 111 to the proximal end 119 and includes an inside surface 114 defining a chamber 116 for retaining fluids. The syringe barrel 100 also includes a distal wall 118 adjacent to the distal end 111 and a flange 120 disposed at the proximal end 119 of the syringe barrel 100. A luer connector 121 is provided in the form of an open tip 122 that extends from the distal wall 118 and includes passageway 124 in fluid connection with the chamber 116. The open tip 122 includes an outside surface 126 that defines an outer cross-sectional dimension and length that is typical of male standard luer connectors.

Figure 2:
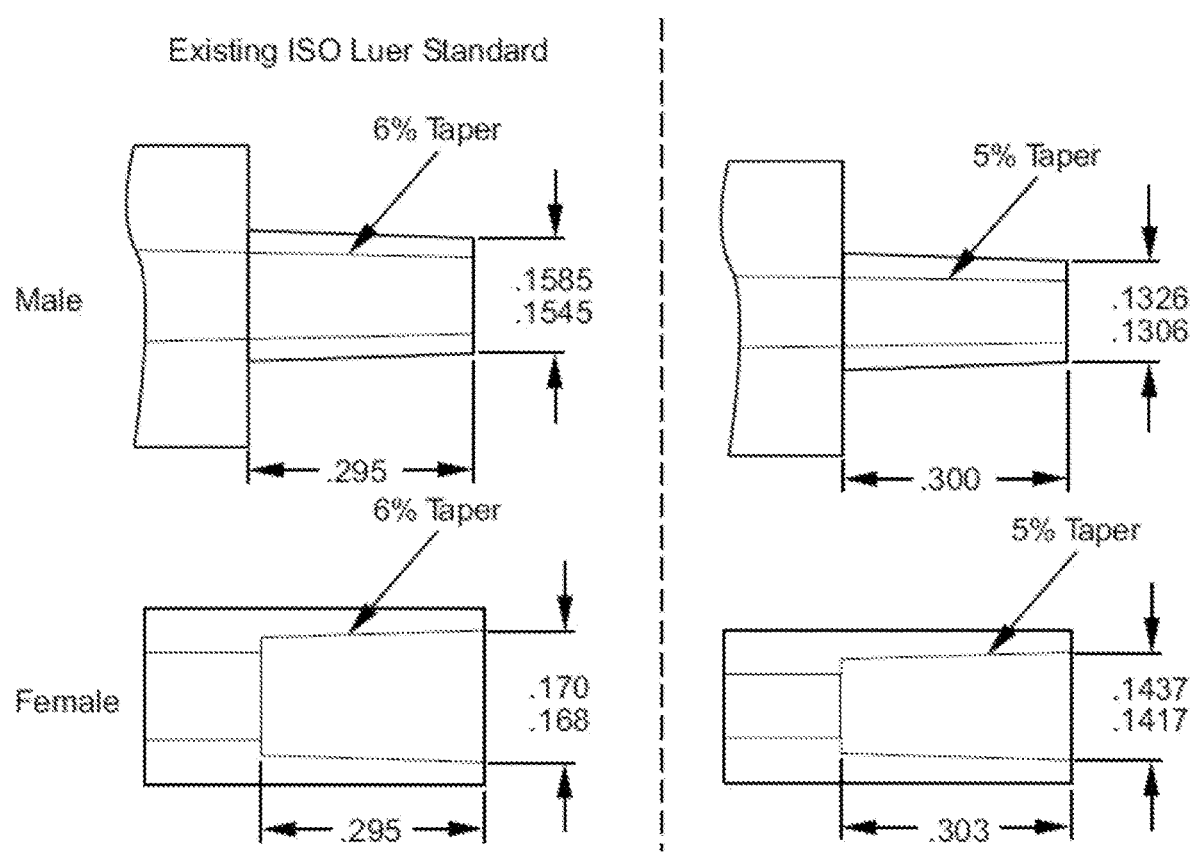
FIG. 2 shows a chart comparing existing ISO standards for standard luer connectors and new standards for male and female connectors in neuraxial applications.

As shown in FIG. 2, a male standard luer tip or standard male connector has specifications as provided by the International Organization for Standardization (ISO) defined in ISO 80369-7, including a 6% taper that increases from the open distal end to the proximal end and an outer cross-sectional diameter at the distal end of the tip measuring between about 0.1545 inches (3.925 mm) and about 0.1570 inches (3.990 mm) for rigid material and between about 0.1545 inches (3.925 mm) and about 0.1585 inches (4.027 mm) for semi-rigid material. A female standard luer hub or female standard luer connector may have a 6% taper that decreases from the open proximal end to the distal end and an inner cross-sectional diameter at the open proximal end measuring between about 0.168 inches (4.270 mm) to about 0.170 inches (4.315 mm). In devices that have female standard luer connectors that incorporate tabs or lugs for connection to a corresponding male luer lock connector, the outer cross-sectional diameter of the female standard luer connector, including the lugs, is in the range from about 0.307 inches (7.80 mm) to about 0.308 inches (7.83 mm). In devices that have female standard luer connectors that do not incorporate tabs or lugs for connection to a corresponding male luer lock connector, the outer cross-sectional diameter may be about 0.224 inches (5.700 mm) for rigid connectors and about 0.265 inches (6.730 mm) for semi-rigid connectors, based on the maximum outside diameter of the female standard luer connector at the base of the lugs of ISO 80369-7. The minimum length of the standard luer tip and/or the standard luer hub is 0.295 inches (7.500 mm), according to ISO 80369-7. As used herein, the phrases "male standard luer connector," "male standard luer tip," "female standard luer hub" and "female standard luer connector" shall refer to connectors having the above dimensions.

Figure 3:
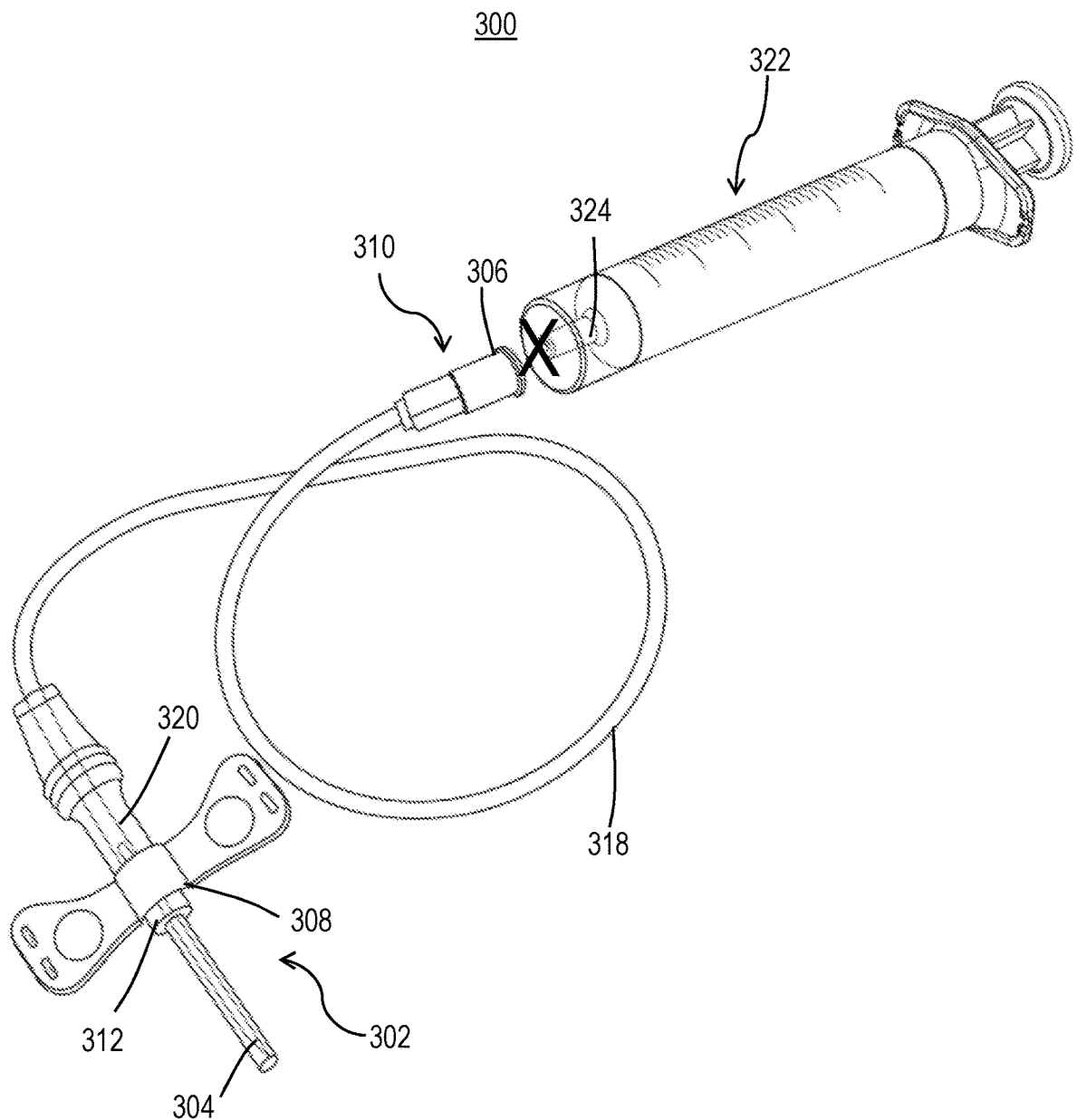
FIG. 3 illustrates a perspective view of a blood collection set showing an incompatible connection between the syringe and a standard luer adapter according to the prior art.

FIG. 3 is a perspective view of a blood collection set 300 showing an incompatible connection between a neuraxial syringe 322 and a female standard luer adapter 306 compliant with ISO 80369-7. The blood collection set 300 in the embodiment shown comprises a catheter assembly 302 including a needle cannula 304 and the female standard luer adapter 306 on opposite ends of the catheter assembly 302. The catheter assembly includes a catheter hub body 320 from which the needle cannula 304 extends from a catheter hub distal end 312. The catheter assembly 302 includes a pair of wings 308, which may be used to adhere the catheter hub body 320 to a patient during a blood collection procedure. In the embodiment shown, a standard luer connector 310 comprising the female standard luer adapter 306 is fluidly connected to the catheter hub body 320 by tubing 318. The neuraxial syringe 322 includes a male neuraxial connector 324 compliant with ISO 80369-6, which is not directly connectable to the female standard luer adapter 306 of the catheter assembly, as indicated by the X between the neuraxial connector 324 and the female standard luer adapter 306.

Figure 4:
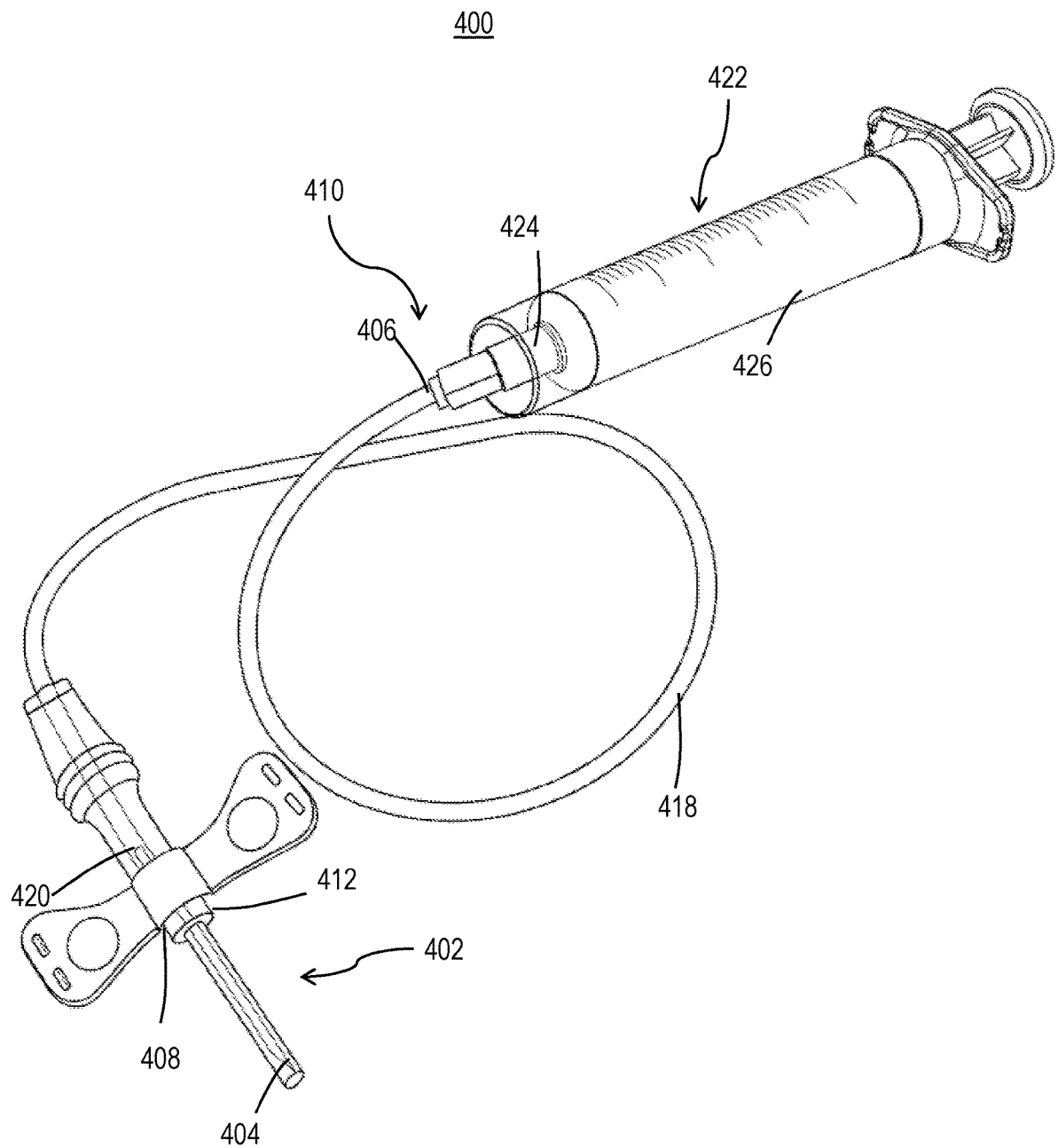
FIG. 4 a perspective view of a blood collection set showing a compatible connection between a neuraxial syringe and a standard luer adapter.

FIG. 4 is a perspective view of a blood collection set 400 including a compatible connection between a syringe 422 having a syringe barrel 426 and a female standard luer adapter 406 compliant with ISO 80369-7. The blood collection set 400 in the embodiment shown comprises a catheter assembly 402 including a needle cannula 404 and the female standard luer adapter 406 on opposite ends of the catheter assembly 402. The catheter assembly 402 includes a catheter hub body 420 from which the needle cannula 404 extends from a catheter hub distal end 412. The catheter assembly 402 includes a pair of wings 408, which may be used to adhere the catheter hub body 420 to a patient during a blood collection procedure. In the embodiment shown, a standard luer connector 410 comprising the female standard luer adapter 406 is fluidly connected to the catheter hub body 420 by tubing 418. The distal end of the syringe barrel 426 includes a male standard luer connector 424 compliant with ISO 80369-7.

Both of the standard luer connectors of the syringe 422 and catheter assembly 402 are sized and shaped to form an interference fit connection and/or fluid-tight engagement with each other. Specifically, the outside surface of the male standard luer connector 424 has a taper, length, and shape that is typical of male standard luer connectors, as described above, that permits syringe 422 to form an interference fit connection with the inside surface of female standard luer adapter 406, which also has a taper, length, and shape that is typical of female standard luer connectors, as also described above. In one or more alternative embodiments, the syringe barrel 426 may include a male standard luer connector in the form of a luer lock connector (not shown), which includes a threaded portion that engages a cooperating structure of the catheter assembly 402, for example, as shown in FIG. 4.

New standards for small bore connectors, for example ISO 80369-6 for neuraxial applications, have caused a need for suitable connectors that do not conform to standard luer connector requirements, i.e. non-luer connectors. As discussed above, these new standards include connectors with a 5% taper, instead of the 6% taper that is currently used with standard luer connectors. In addition, the new standards propose connectors with smaller inner and outer cross-sectional diameters and longer lengths than standard luer connectors. Specifically, under ISO 80369-6, for small bore connectors for liquids and gases in healthcare applications, the taper of the male connector and female connector will be modified from the existing ISO luer standard of 6% to 5% from their proximal ends to the distal ends. For male connectors, the new 5% taper provides a more gradual decrease in the outer cross-sectional dimension of the connector from the proximal end to the open distal end. For female connectors, the new 5% taper provides a more gradual decrease in the inner cross-sectional dimension of the connector from the open proximal end to the distal end, as shown in FIG. 2. In addition, the outer cross-sectional dimension at the open distal end of the male connector will be less than the range of the current ISO luer standard of 0.1545 inches to 0.1585 inches. Specifically, the current proposed ISO standards provide for the outer cross-sectional dimension for the male connector at the open distal end to measure in the range from about 0.1306 inches to about 0.1326 inches. The inner cross-sectional dimension of the female connector at the open proximal end will be less than the range of the current ISO luer standard of 0.168 inches to 0.170 inches. Specifically, the current proposed ISO standards provide for the inner cross-sectional dimension for the female connector at the open proximal end to measure in the range from about 0.1417 inches to about 0.1437 inches. The length of the male connector for neuraxial applications will also be increased from 0.295 inches to about 0.300 inches. The length of female connectors for neuraxial applications will also be increased from 0.295 inches to about 0.303 inches.

The more gradual taper in the new ISO standards for neuraxial applications for both male and female connectors and the smaller outer cross-sectional dimension and inner cross-sectional dimensions of the male and female connectors, respectively, are intended to prevent fluid tight connection of a male connector for a neuraxial application with a female standard luer connector and a female connector for a neuraxial application with a male standard luer connector. However, the smaller outer cross-sectional dimension of the male connector for neuraxial applications at the distal end thereof may make it possible for a user to inadvertently or purposely attach the male connector for neuraxial applications to a female standard luer connector, which may have an inner cross-sectional dimension at its distal end that could accommodate the smaller outer cross-sectional dimension of the male connector for neuraxial applications. The ability to attach the male connector for neuraxial applications to a female standard luer connector, even if not ideal, could allow at least a partial fluid-tight engagement sufficient to deliver unintended fluids or liquids to a patient at an incorrect delivery site.

One or more embodiments provide a medical adapter assembly that will satisfy the misconnection requirements of ISO 80369-6. As used herein the term "medical adapter assembly" is understood to include any structure that is part of a neuraxial device that is capable of making a connection with a secondary neuraxial device. In one or more embodiments, a medical adapter assembly may include an integrated medical device. In other embodiments, a medical adapter assembly may include a collection of device parts.

As used herein, the term "connection-type" refers to the mechanism by which the medical adapter assembly connects to another medical component. Connection-types include but are not limited to slip-type connections and lock-type connections. Slip-type connections are those that use a nominally linear motion to affix a medical device onto a medical adapter assembly. Lock-type connections are those that use primarily a twisting or turning motion to affix a medical device onto a medical adapter assembly. Other medical components to which medical adapter assembly may be connected include, but are not limited, to spinal needle assemblies, epidural needle assemblies, combined spinal and epidural (CSE) needle assemblies, fluid filters, adapters of tubing, and the like.

In one or more embodiments, the medical adapter assembly has two opposing ends. One end of the medical adapter assembly is a non-luer tapered fitting with features to connect to a neuraxial medical device, while the opposing end of the medical adapter assembly is a standard luer fitting with features to connect to a standard luer medical device. The non-luer neuraxial fitting is not directly connectable to a standard luer fitting. In one or more embodiments, the medical adapter assembly includes a check valve that allows fluid flow from the standard luer end to the neuraxial end, while preventing fluid flow from the neuraxial end to the standard luer end.

In one or more embodiments, the check valve is disposed between the non-luer neuraxial end and the luer end. In one or more embodiments, the check valve is integrally formed with the first end and the second end of the medical adapter assembly. The neuraxial fitting and the standard luer fitting may protrude from the check valve.

According to one or more embodiments, the medical adapter assembly will be compliant with ISO 80369-6 and will be able to be utilized for neuraxial applications. As used herein, the term "neuraxial applications" involves the use of medical devices intended to administer medications to neuraxial sites, wound infiltration anesthesia delivery, and other regional anesthesia procedures or to monitor or remove cerebro-spinal fluid for therapeutic or diagnostic purposes. Sites for neuraxial application include the spine, intrathecal or subarachnoid space, ventricles of the brain, and the epi-, extra-, or peri-dural space. Neuraxial application anesthetics can be administered regionally, affecting a large part of the body, such as, for example, the limbs, and include plexus blocks or single nerve blocks. Neuraxial application procedures include continuous infusion of wounds with local anesthetic agents.

According to one or more embodiments, the medical adapter assembly will be utilized for epidural blood patch procedures. As used herein, the phrase "epidural blood patch procedure" refers to a surgical procedure that uses autologous blood (i.e. the patient's own blood) in order to close one or many holes in the dura mater of the spinal cord, usually as a result of a previous lumbar puncture. The epidural blood patch procedure can be used to relieve post dural puncture headaches caused by lumbar puncture (i.e. spinal tap). During an epidural blood patch procedure, a small amount of a patient's blood is injected into the epidural space near the site of the original puncture, and the clotting factors of the blood result in a blood clot which closes the hole in the dura, thus stopping the meningeal leak. The epidural blood patch procedure carries risks associated with any epidural puncture.

One or more embodiments provide a medical adapter assembly that can be connected to neuraxial fittings. As used herein, the term "neuraxial fitting" refers to small-bore, non-luer, connectors that are compliant with ISO 80369-6. In the industry, the neuraxial fitting is referred to as NRFit®. These small-bore connectors, when implemented, help prevent misconnections and misinjections.

Referring to FIGS. 5-8, in one or more embodiments, a medical adapter assembly 500 comprises a first end 502 comprising a neuraxial fitting 504 that is not directly connectable to a standard luer fitting; a second end 506 opposite the first end 502, the second end 506 comprising a standard luer fitting 508 connectable to a standard luer fitting of an intravenous medical device; and a check valve 510 that allows fluid flow from the second end 506 to the first end 502 and prevents fluid flow from the first end 502 to the second end 506.

In one or more embodiments, the neuraxial fitting 504 is a female neuraxial fitting.

In one or more embodiments, the standard luer fitting 508 is a male luer fitting. As used herein, the term "male luer fitting" refers to a medical device fitting have an elongated nozzle and an internally threaded locking ring mounted around the nozzle.

The new ISO 80369-6 standard is intended to eliminate the possibility of misconnection/misinjection between luer and NRFit® systems. Some manufacturers have incorporated features that help to readily distinguish NRFit® from luer fittings, such as coloration and packaging. In the medical industry, the color yellow has been commonly used to indicate a neuraxial route. Thus, in one or more embodiments, the medical adapter assembly 500 is yellow in color.

Figure 5:
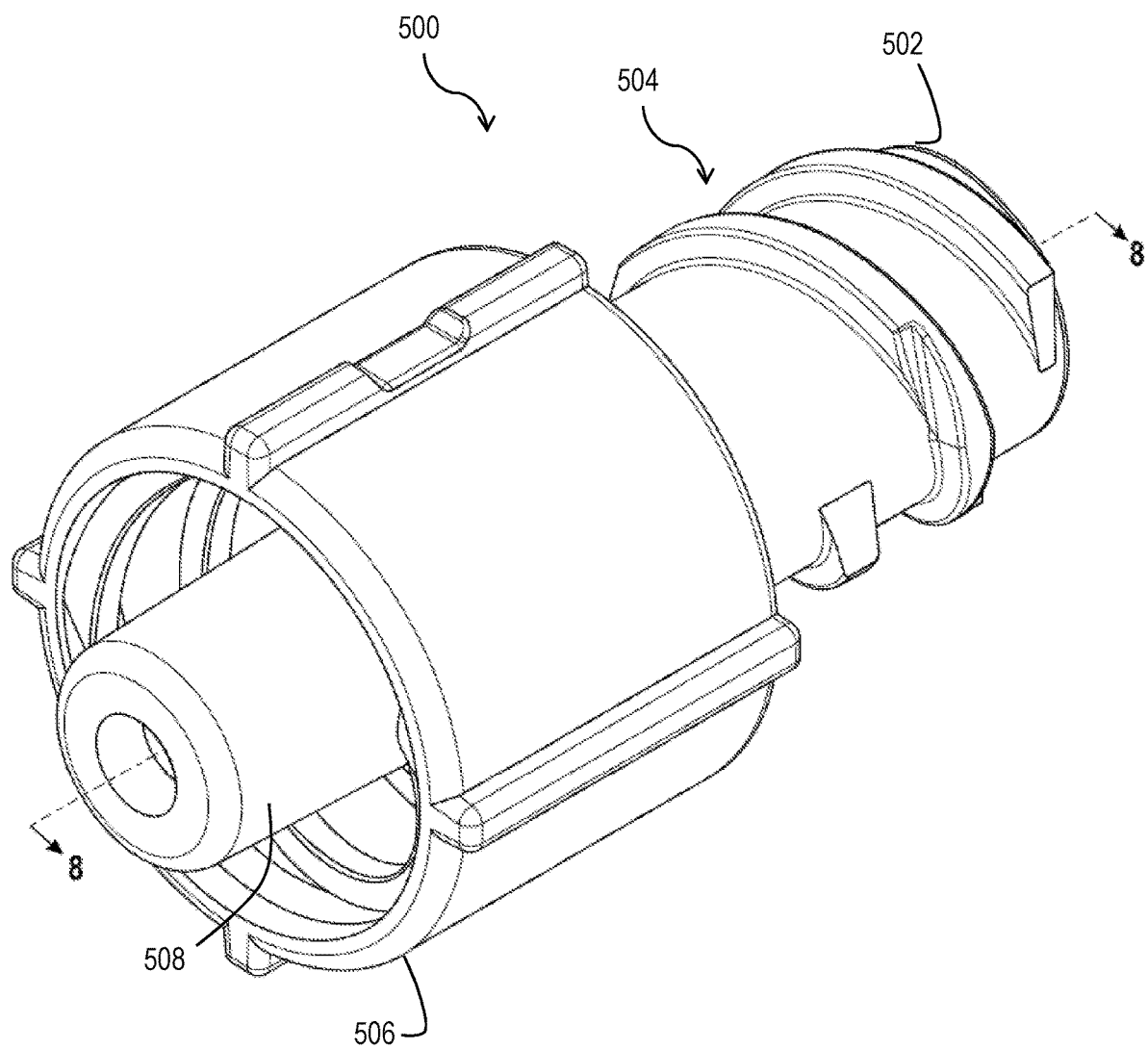
FIG. 5 illustrates a perspective view of a medical adapter assembly according to one or more embodiments.
Figure 6:
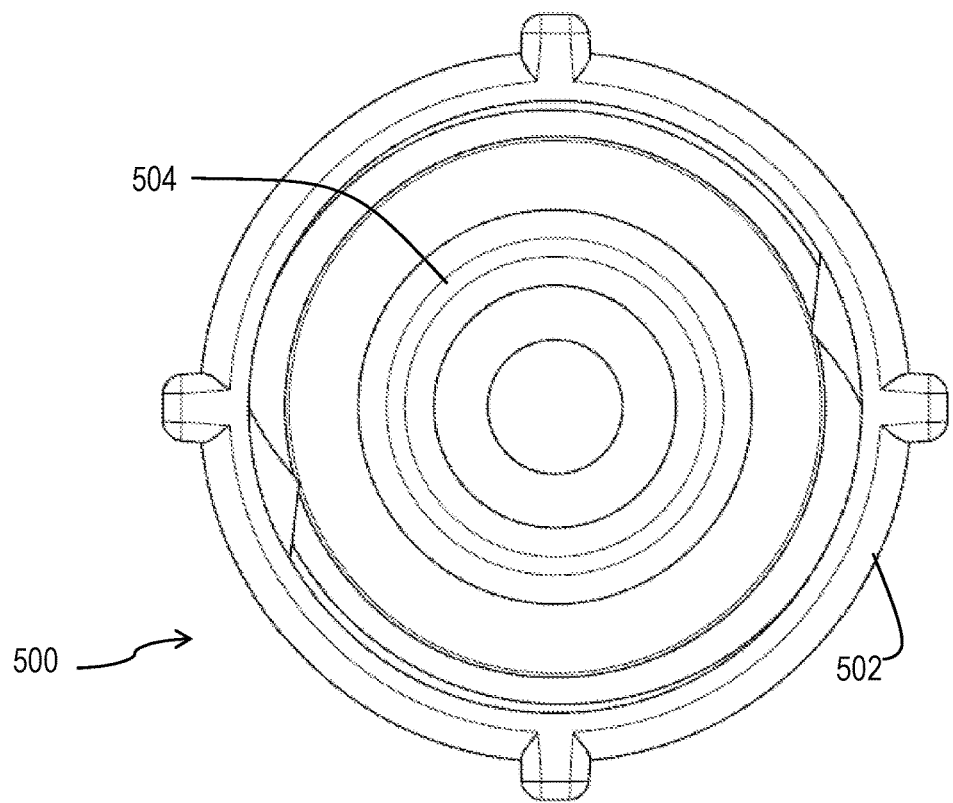
FIG. 6 illustrates a front view of the medical adapter assembly shown in FIG. 5.
Figure 7:
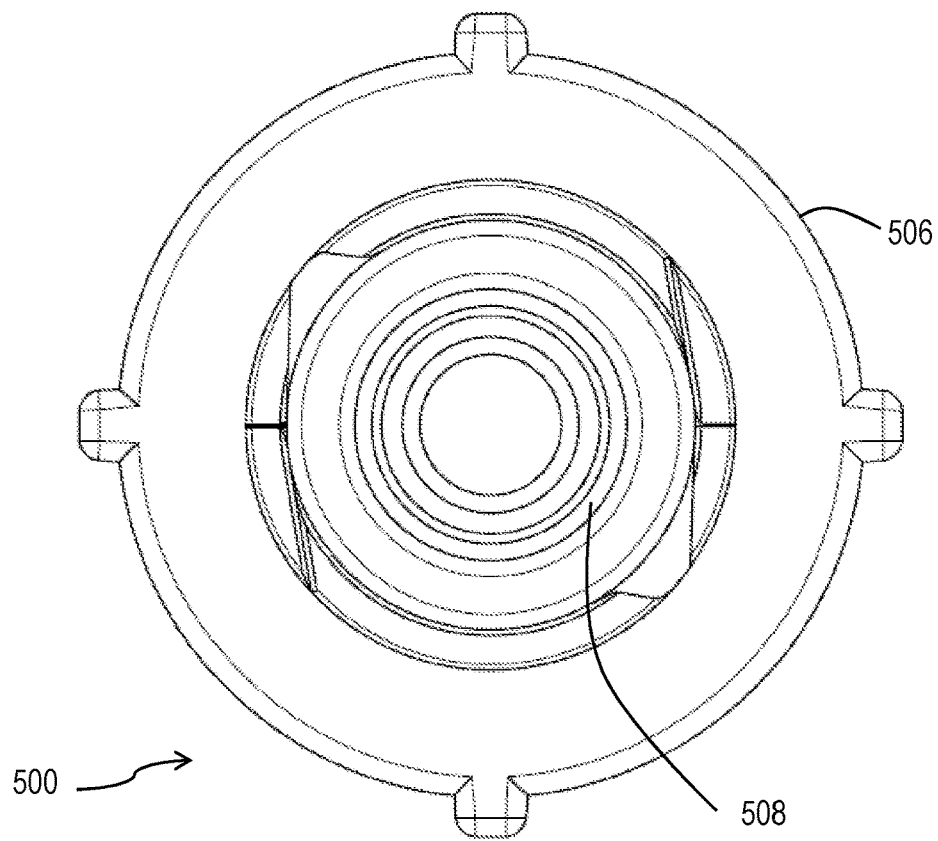
FIG. 7 illustrates a rear view of the medical adapter assembly shown in FIG. 5.

FIG. 6 is a front view the medical adapter assembly shown in FIG. 5. In one or more embodiments, the medical adapter assembly 500 comprises a first end 502 comprising a neuraxial fitting 504 that is not directly connectable to a standard luer fitting. FIG. 7 is a rear view of the medical adapter assembly 500 shown in FIG. 5 the second end 506 opposite the first end 502. In one or more embodiments, the second end 506 comprises a standard luer fitting 508 connectable to a standard luer fitting of an intravenous medical device compliant with 80369-7.

Figure 8:
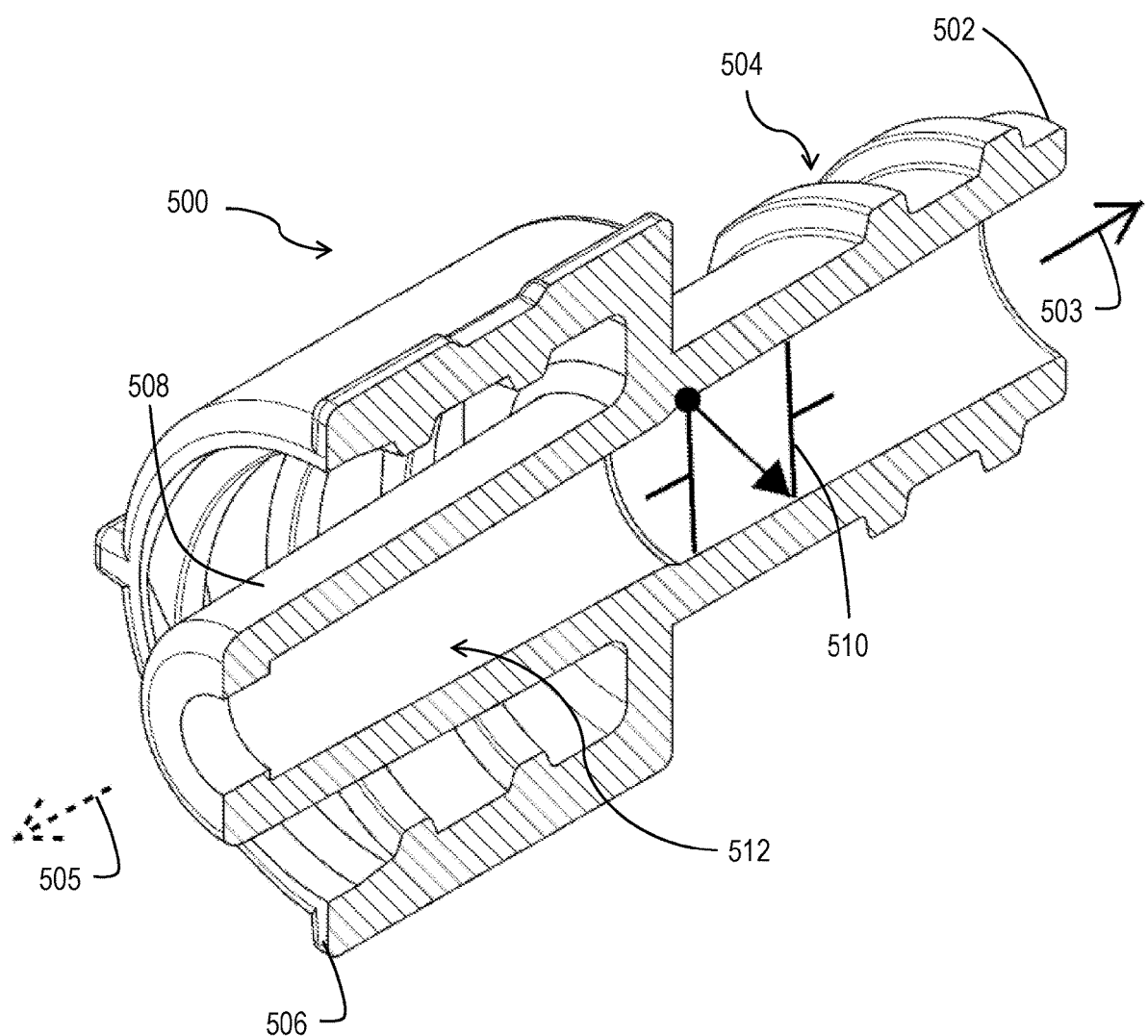
FIG. 8 illustrates a cross-sectional view of the medical adapter assembly taken along line 8-8 of FIG. 6.

FIG. 8 illustrates a cross-sectional perspective view 800 of the medical adapter assembly 500 shown in FIG. 5 and taken along line 8-8. In one or more embodiments, a medical adapter assembly 500 comprises a first end 502 comprising a neuraxial fitting 504 that is not directly connectable to a standard luer fitting; a second end 506 opposite the first end 502, the second end 506 comprising a standard luer fitting 508 connectable to a standard luer fitting of an intravenous medical device; and a check valve 510 that allows fluid flow from the second end 506 to the first end 502 through a channel 512 and prevents fluid flow from the first end 502 to the second end 506. The check valve 510 is shown schematically. As used herein, the term "check valve" refers to two-port valves, which have two openings in the body of the value, one opening for fluid to enter and the other opening for fluid to leave. Check valves work automatically and are not controlled by a patient, medical provider, or caregiver. In one or more embodiments, the check valve is a one-way valve that allows fluid flow in only one direction. In one or more embodiments, the check valve allows fluid flow from the second end 506 of the medical adapter assembly (i.e. the end having the standard luer fitting 508) to the first end 502 (i.e. the end having the neuraxial fitting 504), while preventing fluid flow from the first end 502 of the medical adapter assembly to the second end 506. In one or more embodiments, the fluid flows from the second end 506 through the check valve 510 to the first end 502. The check valve 510 can be any suitable type of check valve used in medical devices to allow fluid to flow in only one direction. Examples of suitable check valves include, but are not limited to a duckbill valve, an umbrella valve, a ball-check valve, a diaphragm check valve, a swing check valve, a stop-check valve, a lift-check valve, and the like. In a specific embodiment, the check valve is selected from one or more of a ball-check valve, a diaphragm check valve, a swing check valve, a stop-check valve, a lift-check valve, and the like.

In one or more embodiments, the check valve 510 is disposed between the first end 502 and the second end 506.

In one or more embodiments, the check valve 510 is integrally formed with the first end 502 and the second end 506. In one or more embodiments, the neuraxial fitting 504 and the standard luer fitting 508 protrude from the check valve 510.

Figure 9:
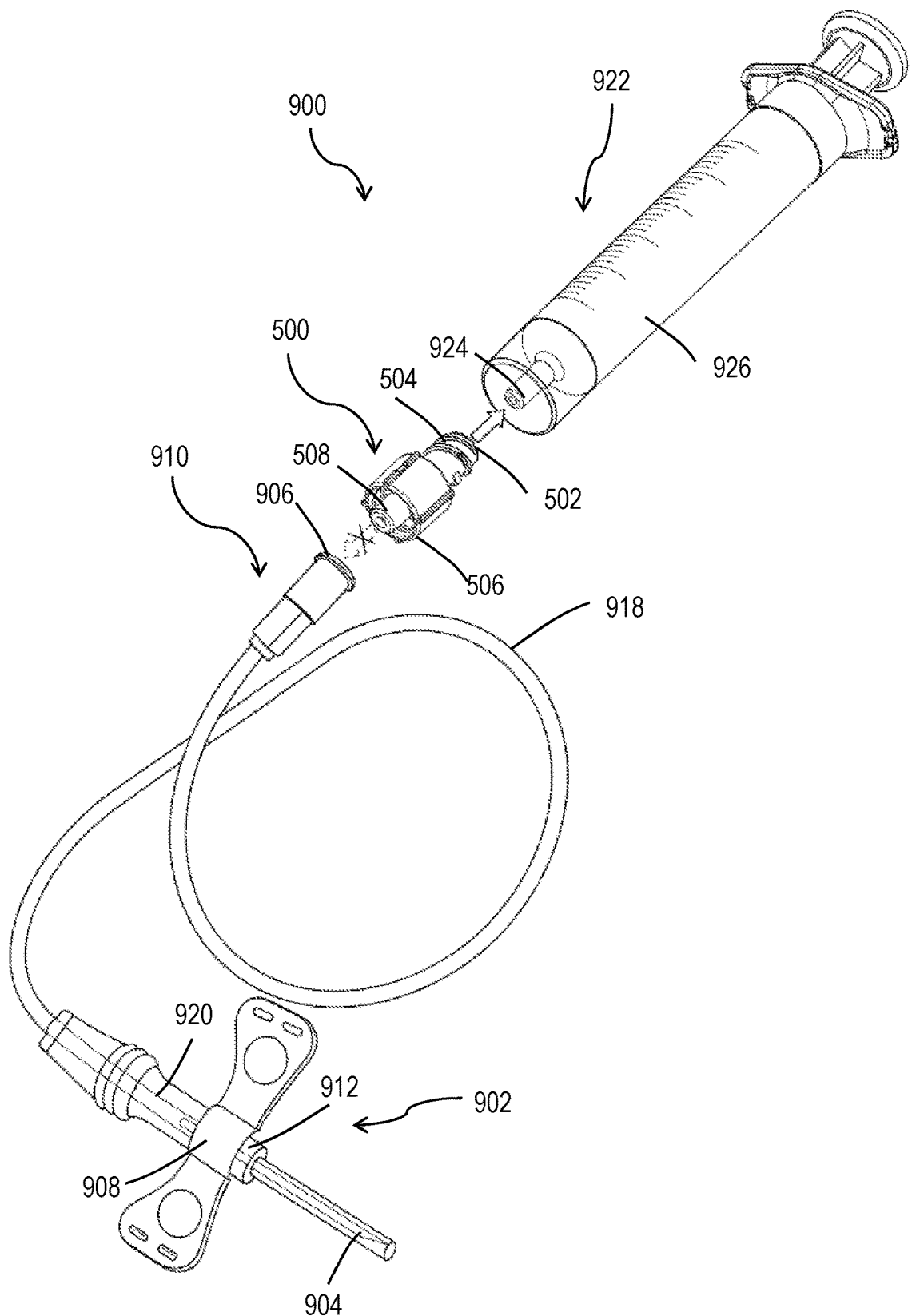
FIG. 9 illustrates an exploded view of a blood collection set including a medical adapter assembly according to one or more embodiments.

FIG. 9 illustrates an exploded view of a blood collection set 900 comprising a medical adapter assembly according to one or more embodiments. The blood collection set 900 in the embodiment shown comprises a catheter assembly 902 including a needle cannula 904 and a female standard luer adapter 906 on opposite ends of the catheter assembly 902. The catheter assembly includes a catheter hub body 920 from which the needle cannula 904 extends from a catheter hub distal end 912. The catheter assembly 902 includes a pair of wings 908, which may be used to adhere the catheter hub body 920 to a patient during a blood collection procedure. In the embodiment shown, a standard luer connector 910 comprising the female standard luer adapter 906 is fluidly connected to the catheter hub body 920 by tubing 918. The neuraxial syringe 922 includes a syringe barrel 926 and a male neuraxial connector 924 compliant with ISO 80369-6, which is not directly connectable to the female standard luer adapter 906 of the catheter assembly 902

Connection of the male neuraxial connector 924 to the female standard luer adapter 906 is enabled by the medical adapter assembly 500 shown with respect to FIGS. 5-8. The medical adapter assembly 500 comprising the first end 502 including a neuraxial fitting 504, a second end 506 opposite the first end 502, the second end 506 comprising a standard luer fitting 508 that is not directly connectable to a neuraxial fitting, and a check valve (shown in FIG. 8) that prevents fluid flow from the first end 502 to the second end 506. As shown in FIG. 9, the first end 502 having the neuraxial fitting 504 of the medical adapter assembly 500 is directly connectable to the male neuraxial connector 924 compliant with ISO 80369-6 of the syringe barrel 926. Thus, as shown, the catheter assembly 902 is not compatible with neuraxial syringe 922 of the illustrated blood collection set 900 without the medical adapter assembly 500 of the present disclosure.

Figure 10:
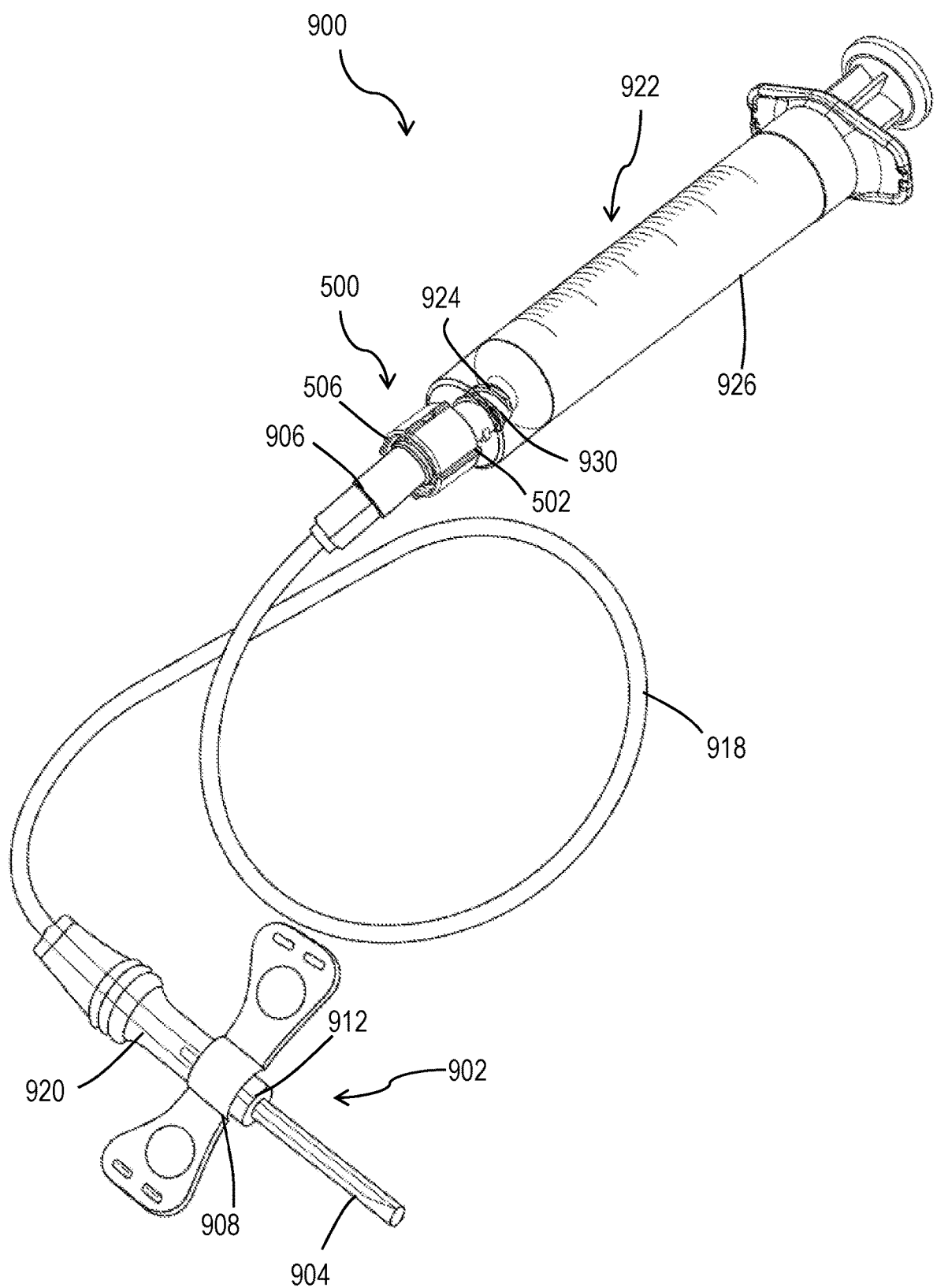
FIG. 10 illustrates the blood collection set of FIG. 9 in an assembled configuration according to one or more embodiments.

FIG. 10 illustrates the blood collection set shown in FIG. 9 in an assembled configuration according to one or more embodiments. The blood collection set 900 in the embodiment shown comprises a catheter assembly 902 including a needle cannula 904 and a female standard luer adapter 906 on opposite ends of the catheter assembly 902. The catheter assembly 902 includes a catheter hub body 920 from which the needle cannula 904 extends from a catheter hub distal end 912. The catheter assembly 902 includes a pair of wings 908, which may be used to adhere the catheter hub body 920 to a patient during a blood collection procedure. In the embodiment shown, a standard luer connector 910 comprising the female standard luer adapter 906 is fluidly connected to the catheter hub body 920 by tubing 918. The neuraxial syringe 922 includes a syringe barrel 926 and a male neuraxial connector 924 compliant with ISO 80369-6, which is not directly connectable to the female standard luer adapter 906 of the catheter assembly 902

Connection of the male neuraxial connector 924 to the female standard luer adapter 906 is enabled by the medical adapter assembly 500 shown with respect to FIGS. 5-8. The medical adapter assembly 500 comprising the first end 502 including a neuraxial fitting 504, a second end 506 opposite the first end 502, the second end 506 comprising a standard luer fitting 508 that is not directly connectable to a neuraxial fitting, and a check valve (shown in FIG. 8) that prevents fluid flow from the first end 502 to the second end 506. As shown in FIG. 10, the first end 502 having the neuraxial fitting 504 of the medical adapter assembly 500 is connected to the male neuraxial connector 924 compliant with ISO 80369-6 of the syringe barrel 926.

A second aspect of the present disclosure is directed to a method. Referring to FIG. 10, in one or more embodiments, a method comprises connecting a neuraxial syringe 922 comprising a syringe barrel 926 and a male neuraxial connector 924 that is not directly connectable to (i.e. compliant with ISO 80369-6) a standard luer connector 910 comprising the female standard luer adapter 906 to a medical adapter assembly 500. The medical adapter assembly 500 has a first end 502 comprising a neuraxial fitting 504, a second end 506 opposite the first end 502, the second end 506 comprising a standard luer fitting 508 that is not directly connectable to a neuraxial fitting, and a check valve 510 (as shown in FIG. 8) that prevents fluid flow from the first end 502 to the second end 506 as indicated by the dashed arrow 505 but permits fluid flow in the direction of arrow 503 (as shown in FIG. 8). The method then comprises disconnecting the medical adapter assembly 500 from the neuraxial syringe 922, and connecting the neuraxial fitting 504 of the medical adapter assembly 500 to a neuraxial needle (not shown).

In one or more embodiments, the method further comprises drawing blood from a patient's epidural space into the syringe barrel 926. In one or more embodiments, the method further comprises performing an epidural blood patch procedure.

In one or more embodiments, the method further comprises disinfecting the distal tip 930 of the neuraxial syringe 922 prior to connecting the distal tip 930 of the neuraxial syringe 922 to the neuraxial fitting of the neuraxial needle. In one or more embodiments, the neuraxial needle is selected from a spinal needle or an epidural needle.

A third aspect of the present disclosure is directed to a kit. In one or more embodiments, the kit includes a medical adapter assembly, a syringe, and a needle. In one or more embodiments, the medical adapter assembly in the kit comprises a first end comprising a neuraxial fitting that is not directly connectable to a standard luer fitting; a second end opposite the first end, the second end comprising a standard luer fitting connectable to a standard luer fitting of an intravenous medical device; and a check valve that allows fluid flow from the second end to the first end and prevents fluid flow from the first end to the second end. In one or more embodiments, the syringe in the kit comprises a distal tip with a neuraxial fitting that is not directly connectable to a standard luer fitting. In one or more embodiments, the needle in the kit is adapted to deliver medication to the epidural space.

The components of the medical adapter assembly and the kit of one or more embodiments may be fabricated of a variety of materials suitable for medical and health care applications. For example, medical adapter assembly may be fabricated from a medical-grade material, such as, but not limited to, nylon, polypropylene, polycarbonate, polyvinylidene fluoride, acrylonitrile butadiene styrene, and polyvinyl chloride. The syringe may be fabricated from a medical-grade material, such as, but not limited to, nylon, polypropylene, polycarbonate, polyvinylidene fluoride, acrylonitrile butadiene styrene, and polyvinyl chloride. In a specific embodiment, the syringe is fabricated from one or more of polypropylene or polycarbonate.

In one or more embodiments, the kit further comprises an epidural catheter. In one or more embodiments, the kit further comprises a thread assist guide. In one or more embodiments, the kit further comprises an epidural flat filter. In one or more embodiments, the kit is an epidural kit.

Reference throughout this specification to "one embodiment," "certain embodiments," "one or more embodiments" or "an embodiment" means that a particular feature, structure, material, or characteristic described in connection with the embodiment is included in at least one embodiment of the disclosure. Thus, the appearances of the phrases such as "in one or more embodiments," "in certain embodiments," "in one embodiment" or "in an embodiment" in various places throughout this specification are not necessarily referring to the same embodiment of the disclosure. Furthermore, the particular features, structures, materials, or characteristics may be combined in any suitable manner in one or more embodiments.

Although the disclosure herein has been described with reference to particular embodiments, it is to be understood that these embodiments are merely illustrative of the principles and applications of the present disclosure. It will be apparent to those skilled in the art that various modifications and variations can be made to the method and apparatus of the present disclosure without departing from the spirit and scope of the disclosure. Thus, it is intended that the present disclosure include modifications and variations that are within the scope of the appended claims and their equivalents.

What is claimed is:

1. An autologous blood collection set comprising:
   a medical adapter comprising:
      a first end comprising a neuraxial fitting that is not directly connectable to a standard luer fitting and is removably connectable to a neuraxial fitting of a neuraxial syringe;
      a second end opposite the first end, the second end comprising a standard luer fitting connectable to a standard luer fitting of an intravenous medical device; and
      a check valve that allows fluid flow only from the second end to the first end and prevents fluid flow from the first end to the second end; and
   a catheter adapter assembly including a needle cannula and a luer adapter connectable to the second end of the medical adapter, the autologous blood collection set configured to be used in an epidural blood patch procedure.

2. The autologous blood collection set of claim 1, wherein the check valve is disposed between the first end and the second end.

3. The autologous blood collection set of claim 2, wherein the check valve is integrally formed with the first end and the second end.

4. The autologous blood collection set of claim 3, wherein the neuraxial fitting of the first end and the standard luer fitting of the second end protrude from the check valve.

5. The autologous blood collection set of claim 1, wherein the neuraxial fitting of the first end is a female neuraxial fitting.

6. The autologous blood collection set of claim 1, wherein the standard luer fitting of the second end is a male luer fitting.

7. The autologous blood collection set of claim 1, wherein the check valve is a one-way valve selected from the group consisting of a duckbill valve, an umbrella valve, a ball-check valve, a diaphragm check valve, a swing check valve, a stop-check valve, or a lift-check valve.

8. The autologous blood collection set of claim 7, wherein the one-way valve is a ball-check valve, a diaphragm check valve, a swing check valve, a stop-check valve, or a lift-check valve.

9. The autologous blood collection set of claim 1, wherein the medical adapter is yellow in color.

10. The autologous blood collection set of claim 1, wherein the check valve is not controllable by a patient, medical provider or a care-giver.

11. The autologous blood collection set of claim 1, wherein the autologous blood collection set is configured so that when the autologous blood collection set is used in the epidural blood patch procedure, autologous blood can be delivered from the neuraxial syringe only after the medical adapter has been disconnected from the neuraxial syringe.

12. A kit comprising:
   the autologous blood collection set of claim 1; and
   a neuraxial syringe comprising a distal tip including a neuraxial fitting that is not directly connectable to a standard luer fitting.

13. The kit of claim 12, further comprising one of spinal needle and an epidural needle.

14. The kit of claim 12, further comprising a thread assist guide.

15. The kit of claim 12, further comprising an epidural flat filter.

* * * * *